United States Patent
Potyrailo et al.

(10) Patent No.: US 6,626,025 B2
(45) Date of Patent: Sep. 30, 2003

(54) DEVICES AND METHODS FOR HIGH THROUGHPUT SCREENING OF ABRASION RESISTANCE OF COATINGS

(75) Inventors: Radislav Alexandrovich Potyrailo, Niskayuna, NY (US); Bret Ja Chisholm, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 420 days.

(21) Appl. No.: 09/770,006

(22) Filed: Jan. 26, 2001

(65) Prior Publication Data

US 2002/0103605 A1 Aug. 1, 2002

(51) Int. Cl.⁷ ................................................. G01N 3/56
(52) U.S. Cl. .................................. 73/7; 73/579; 702/22
(58) Field of Search ............................... 73/7, 570, 574, 73/579, 584, 589; 702/22

(56) References Cited

U.S. PATENT DOCUMENTS

| | | | |
|---|---|---|---|
| 5,488,866 A | * 2/1996 | Ravel et al. | 73/579 |
| 6,137,708 A | * 10/2000 | Lin et al. | 365/51 |
| 6,287,765 B1 | * 9/2001 | Cubicciotti | 435/6 |
| 6,318,147 B1 | * 11/2001 | Steinruck et al. | 73/7 |
| 6,438,497 B1 | * 8/2002 | Mansky et al. | 702/22 |
| 6,439,765 B2 | * 8/2002 | Smith | 374/31 |
| 6,490,928 B2 | * 12/2002 | Moser | 73/627 |

OTHER PUBLICATIONS

"Standard Test Method for Resistance of Transparent Plastics to Surface Abrasion", ASTM D 1044–94, ASTM: 1994.
"Standard Test Method for Haze and Luminous Transmittance of Transparent Plastics", ASTMD 1003–97, ASTM: 1997.
"Recognition and Quantitation of Closely Related Chlorinated Organic Vapors with Acoustic Wave Chemical Sensor Arrays", by R.A. Potyrailo et al., Proc. SPIE–Int. Soc. Opt. Eng., 3856 (Internal Standardization and Calibration Architectures for Chemical Sensors) 80–87 (1999).
"Field Evaluation of Acoustic Wave Chemical Sensors for Monitoring of Organic Solvents in Groundwater", by R.A. Potyrailo et al., Proc. SPIE–Int. Soc. Opt. Eng., 3856 (Internal Standardization and Calibration Architectures for Chemical Sensors) 140–147 (1999).

* cited by examiner

*Primary Examiner*—Hezron Williams
*Assistant Examiner*—Charles Garber
(74) *Attorney, Agent, or Firm*—Andrew J. Caruso; Patrick K. Patnode (57) ABSTRACT

A device and method for the high throughput screening of the abrasion resistance of coatings. The device includes a plurality of transducers, each of the plurality of transducers having at least one external surface, and a plurality of coatings, each of the plurality of coatings deposited onto the external surface(s) of one of the plurality of transducers. The device also includes a plurality of oscillation sources, coupled to the plurality of transducers, for generating and applying an oscillation potential to each of the plurality of transducers. Further, the device includes a plurality of oscillation detectors, coupled to the plurality of transducers, for measuring the oscillation frequency and a variation in oscillation frequency associated with abrasion resistance in each of the plurality of transducers. The method includes exposing each of the plurality of coatings to an abrasive material, the abrasive material causing a change in mass and/or viscoelastic property in each of the plurality of coatings. Further, the method includes detecting and measuring the oscillation parameters and a variation in oscillation parameters in each of the plurality of transducers, wherein the variation in oscillation parameters corresponds to the change in mass in each of the plurality of coatings.

43 Claims, 5 Drawing Sheets fig 1 fig. 2 fig 3 fig. 4 fig. 5

DEVICES AND METHODS FOR HIGH THROUGHPUT SCREENING OF ABRASION RESISTANCE OF COATINGS

The U.S. Government may have certain rights in this invention pursuant to NIST contract number 70NANB9H3038.

BACKGROUND OF THE INVENTION

This invention relates generally to devices and methods for screening arrays of coatings and, more specifically, to devices and methods for the comparative evaluation of the abrasion resistance of coating samples comprising a coating array.

Due to the complex nature of coatings, such as protective/decorative coatings, barrier coatings, adhesive/release coatings, optic transparent coatings, anticorrosive coatings, electric conductive coatings, and scratch resistant coatings, it is difficult to predict coating performance using basic scientific principles. As a result, the formulation of an effective coating commonly requires extensive experimentation. To accelerate the coating development process, automation of the production of coating samples, miniaturization of these coating samples, and high throughput screening of important coating properties are highly desirable.

An important consideration in the development of coatings, especially those used for the protection of plastic substrates, is abrasion resistance. A typical method for measuring abrasion resistance is the measurement of haze. In this method, a relatively large area of coating, about 1 $cm^2$, is measured, using optical interrogation techniques, to quantify transmitted and diffused, or scattered, light. Haze is the ratio of scattered light to transmitted light. This method, however, has several important shortcomings that limit its applicability to the high throughput screening of combinatorial libraries, including: 1) the requirement of having large coating areas for measurement; 2) the inability to obtain reliable haze measurements of less than 1%; 3) the inability to measure abrasion resistance in optically transparent coatings on a substrate; 4) the inability to rapidly measure multiple samples; and 5) difficulty in measurement automation.

Therefore, there is a need for automated, high throughput devices and methods for screening arrays of coatings for abrasion resistance. Further, there is a need for devices and methods for measuring abrasion resistance that are sensitive and that require only small coating samples for accurate measurement.

BRIEF SUMMARY OF THE INVENTION

Thus, the present invention provides devices and methods for the high throughput screening of the abrasion resistance of coatings.

A device of one embodiment for the high throughput screening of the abrasion resistance of coatings includes a plurality of transducers, each of the plurality of transducers having at least one external surface, and a plurality of coatings, each of the plurality of coatings deposited onto the external surface(s) of one of the plurality of transducers. Further, the device includes a plurality of oscillation sources, coupled to the plurality of transducers, operable for generating and applying an oscillation potential to each of the plurality of transducers. Finally, the device includes a plurality of oscillation detectors, coupled to the plurality of transducers, operable for measuring the oscillation frequency and variation in oscillation frequency in each of the plurality of transducers. Each of the plurality of coatings is exposed to an abrasive material causing a change in mass in each of the plurality of coatings. This change in mass results in a variation in oscillation frequency in each of the plurality of transducers.

A method of one embodiment for the high throughput screening of the abrasion resistance of coatings includes providing a plurality of transducers, each of the plurality of transducers having at least one external surface, and depositing a plurality of coatings onto the external surface(s) of the plurality of transducers, each of the plurality of coatings deposited onto the external surface(s) of one of the plurality of transducers. Further, the method includes generating and applying an oscillation potential to each of the plurality of transducers. The method also includes exposing each of the plurality of coatings to an abrasive material, the abrasive material causing a change in mass in each of the plurality of coatings. Finally, the method includes detecting and measuring the oscillation parameters and variation in oscillation parameters in each of the plurality of transducers, wherein a first oscillation parameter corresponds to an unabraded coating and a second oscillation parameter corresponds to an abraded coating, the variation in oscillation parameter corresponding to the change in mass and/or viscoelastic property in each of the plurality of coatings.

DETAILED DESCRIPTION OF THE INVENTION

Figure 1:
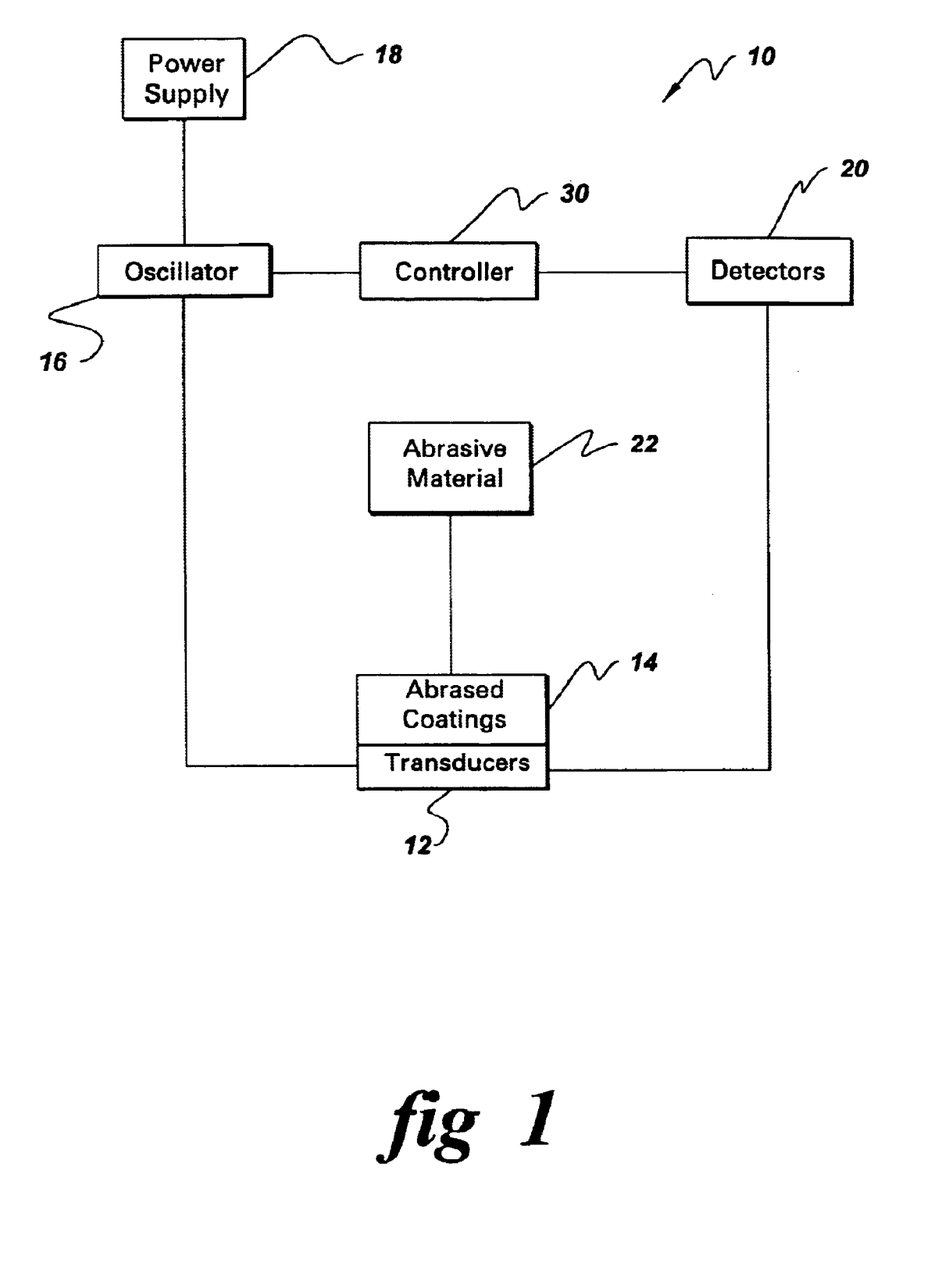
FIG. 1 is a schematic diagram of a device for the high throughput screening of the abrasion resistance of arrays of coatings.

FIG. 1 is a schematic diagram of a device for the high throughput screening of the abrasion resistance of arrays of coatings. Referring to FIG. 1, the device 10 includes a plurality of transducers 12, each of the plurality of transducers 12 having at least one external surface. Preferably, the transducers 12 include a piezoelectric substrate oscillating in a thickness-shear mode. The device 10 also includes a plurality of coatings 14, each of the plurality of coatings 14 deposited onto the external surface(s) of one of the plurality of transducers 12. The coatings 14 may include, for example, mixtures of partially hydrolyzed/condensed alkoxy silanes and colloidal silica; mixtures of acrylates, reactively modified colloidal silica and photoinitiator; mixtures of oligomers or monomers containing isocyanate groups and oligomers or monomers containing hydroxyl, amino, or carboxylic acid groups; mixtures of oligomers or monomers containing hydroxyl or N-methylol groups or N-methylol ether groups and oligomers or monomers containing N-methylol groups or N-methylol ether groups or carboxylic acid groups; mixtures of oligomers or monomers containing epoxide groups and oligomers or monomers containing hydroxyl, amino, carboxylic acid, or anhydride groups; etc., each further mixed with a solvent and various additives. Further, the device 10 includes a plurality of oscillation sources 16, coupled to the plurality of transducers 12, operable for generating and applying an oscillation potential to each of the plurality of transducers 12. Preferably, the oscillation sources 16 include electrodes attached to a power source 18, providing an oscillating potential and inducing oscillation in the transducers 12. Finally, the device 10 includes a plurality of oscillation detectors 20, coupled to the plurality of transducers 12, operable for measuring a first oscillation frequency, a second oscillation frequency, and a variation in oscillation frequency in each of the plurality of transducers 12. The oscillation detectors 20 may be, for example, a plurality of frequency counters.

In operation, each of the plurality of coatings 14 is exposed to an abrasive material 22, such as Sundance Art Glass (Mountain View, Calif.), SAND-100 MESH high grade silica, glass beads, black silicon carbide abrasive powder, boron carbide, diamond powder, aluminum oxide, silicon oxide, garnet, steel grit, walnut shell, sodium bicarbonate, sesquicarbonate, or slurry, causing a change in mass in each of the plurality of coatings 14. This change in mass results in a variation in oscillation frequency in each of the plurality of transducers 12, providing a quantification of the abrasion resistance of the samples of a coating array that may be, for example, correlated to haze values. Optionally, in another detection mode, changes in the viscoelastic properties of the plurality of coatings 14, resulting from the distortion of the coatings 14, may be correlated to measurements of abrasion resistance.

Figure 2:
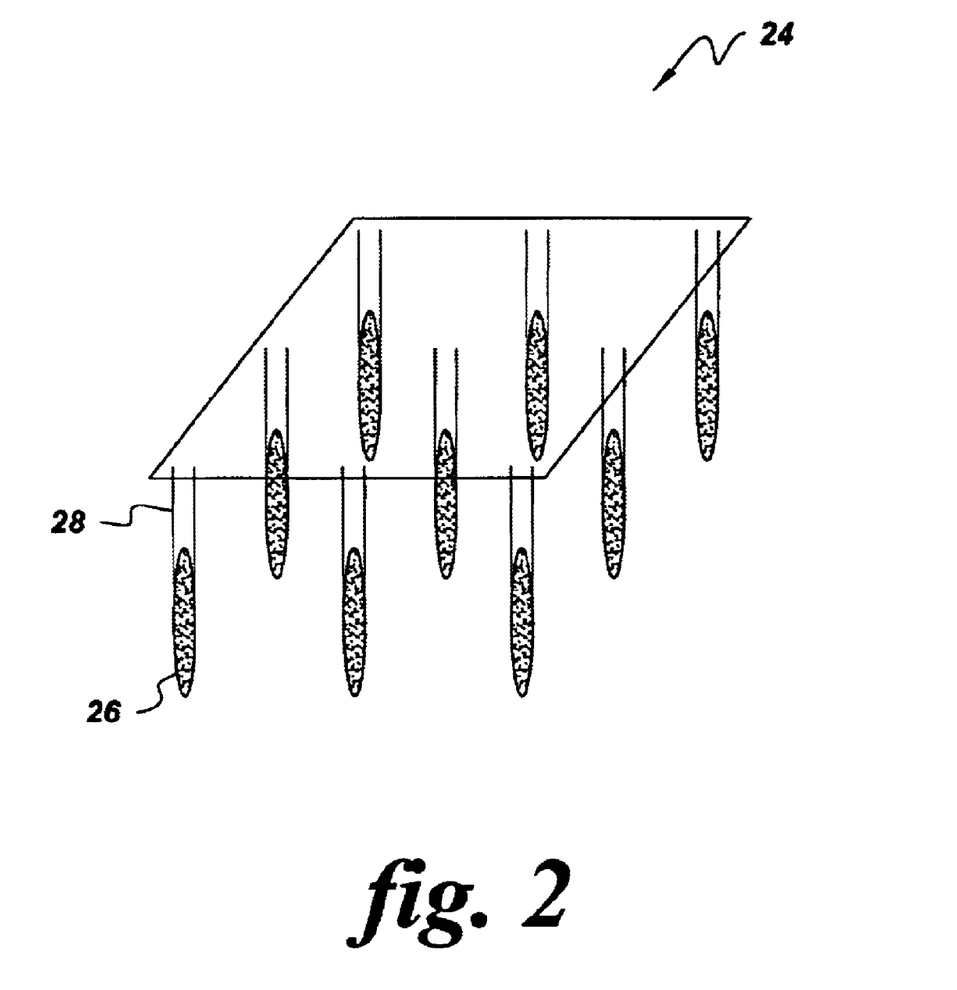
FIG. 2 is a schematic diagram of the transducer set up of the device for the high throughput screening of the abrasion resistance of arrays of coatings.

FIG. 2 is a schematic diagram of the transducer set up of the device for the high throughput screening of the abrasion resistance of arrays of coatings. Referring to the transducer set up 24 of FIG. 2, the measurement of the change in mass of a coating subjected to abrasion testing requires the rapid detection of the removal of minute quantities of material from the surface of an acoustic-wave transducer 26. Preferably, this acoustic-wave transducer 26 comprises a substrate oscillating in a thickness-shear mode, i.e. a thickness-shear mode (TSM) device. One type of TSM device is a quartz crystal microbalance (QCM). These devices are typically ⅛–2 in. in diameter and 50 μm to 0.1 mm in thickness. An oscillating potential is applied to electrodes 28 deposited onto two opposite sides of the quartz crystal. As a result, the crystal oscillates in the thickness-shear mode with a fundamental frequency that may be measured using a conventional frequency counter. The oscillation in the TSM transducer may be measured before and after a coating covering the TSM transducer is exposed to an abrasive material and, taking into account such factors as the dimensions and parameters of the crystal, the coating density, and the measurement temperature, correlated to a change in mass in the coating. When a coating deposited onto an acoustic-wave transducer 26 is exposed to an abrasive material of interest, the coating experiences a degree of mass loss that depends upon its abrasion resistance.

The change in mass of the oscillating crystal of a TSM transducer is determined from the change in resonant frequency of the crystal according to the Sauerbrey equation, $$\Delta f = -2f_0^2 (m/A)(\mu_Q \rho_Q)^{-1/2} \tag{1}$$

where $\Delta f$ is the change in resonant frequency upon material deposition or removal, $f_0$ is the fundamental resonant frequency of the unloaded device, $\mu_Q$ is the shear modulus of the piezoelectric substrate, $\mu_Q$ is the piezoelectric substrate density, m is the total mass of the material deposited onto both faces of the crystal, and A is the active surface area of one face of the crystal.

In one embodiment of the present invention, the acoustic-wave transducers 26 used were 10-MHz AT-cut quartz crystals with an active electrode area of 0.2 cm². The mass sensitivity of a crystal per unit frequency change is, $$m/\Delta f = -A/(2f_0^2)(\mu_Q \rho_Q)^{-1/2} \tag{2}$$

The minus sign indicates that, upon mass increase, the oscillation frequency decreases, while upon mass decrease, the oscillation frequency increases. For this embodiment, $\mu_Q = 2.947 \times 10^{11}$ g·cm$^{-1}$·s$^{-2}$ and $\rho_Q = 2.648$ g·cm$^{-3}$. Thus, the mass sensitivity is, $$m/\Delta f = -0.883 \times 10^{-9} \text{ g·Hz}^{-1} \tag{3}$$

The above relationship demonstrates that the TSM transducer of this embodiment of the present invention is able to detect a mass change of 0.883 ng when the frequency measurement resolution is 1 Hz, a typical frequency measurement noise level. The mass sensitivity is improvable when adequate gate time and temperature stabilization are utilized for frequency measurements. For example, in this case, the noise in frequency measurements is reducible to 0.05 Hz, which provides mass resolution of 44 pg. The mass sensitivity of such measurements is thus approximately six orders of magnitude higher than conventional laboratory scale balances.

Other types of acoustic-wave devices and mechanical resonators may be adapted for the various applications described in connection with the present invention, as well as others, as is understood by those familiar with the art. For example, high (1 MHz–70 MHz) and low (100+Hz-1+MHz) frequency bulk acoustic wave devices, or thickness shear mode resonators, may be used to measure the abrasion resistance of coatings. Suitable devices also include, but are not limited to, surface acoustic wave devices, Lamb wave (LW) devices, flexural plate wave devices, acoustic plate mode (APM) devices, Love wave devices, bimorphs, unimorphs, cantilevers, torsion resonators, tuning forks, membrane resonators, etc.

Referring again to FIG. 1 and as discussed above, the device 10 includes a plurality of coatings 14, each of the plurality of coatings 14 deposited onto the external surface (s) of one of the plurality of transducers 12. The coatings 14 may include, for example, mixtures of partially hydrolyzed/ condensed alkoxy silanes, colloidal silica, solvent, and various additives; mixtures of acrylates, reactively modified colloidal silica, photoinitiator, solvent, and various additives; mixtures of oligomers or monomers containing isocyanate groups, oligomers or monomers containing hydroxyl, amino, or carboxylic acid groups, solvent, and various additives; mixtures of oligomers or monomers containing hydroxyl or N-methylol groups or N-methylol ether groups, oligomers or monomers containing N-methylol groups or N-methylol ether groups or carboxylic acid groups, solvent, and various additives; mixtures of oligomers or monomers containing epoxide groups, oligomers or monomers containing hydroxyl, amino, carboxylic acid, or anhydride groups, solvent, and various additives; etc. The coatings 14 may be applied to the plurality of transducers 12 by dip-coating, spray-coating, spin-coating, brushing, or vapor deposition, among other methods. Each of these coatings 14 is exposed to an abrasive material 22, causing a change in mass in each of the coatings 14. Preferably, each sample of an array of coatings is exposed equally to the abrasive material 22 so that comparative evaluations of abrasion resistance may be made. Alternatively, a comparative screening may be performed by exposing each of the coatings 14 to different amounts of an abrasive material 22. As discussed above, suitable examples of abrasive materials 22 include Sundance Art Glass (Mountain View, Calif.), SAND-100 MESH high grade silica, glass beads, black silicon carbide abrasive powder, boron carbide, diamond powder, aluminum oxide, silicon oxide, garnet, steel grit, walnut shell, sodium bicarbonate, sesquicarbonate, and slurries.

The device 10 also includes a plurality of oscillation sources 16, coupled to the plurality of transducers 12, operable for generating and applying an oscillation potential to each of the plurality of transducers 12. Preferably, the oscillation sources 16 include electrodes attached to a power source 18, providing an oscillating potential and inducing oscillation in the transducers 12. The power source may be an internal or external power supply, such as a 5 volt battery. Preferably, a single power source 18 is connected to the plurality of transducers 12. The plurality of oscillation detectors 20, coupled to the plurality of transducers 12 and operable for measuring a first and second oscillation frequency and a variation in oscillation frequency in each of the plurality of transducers 12, may be, for example, a plurality of frequency counters. The first oscillation frequency corresponds to an unabraded coating 14 and the second oscillation frequency corresponding to an abraded coating 14. The plurality of oscillation detectors 20 may also be a single frequency counter coupled with a multiplexer and a controller 30, allowing for the sequential measurement of oscillation frequency in each transducer 12 using a single device. For example, the device 10 may include a 225-MHz Universal Counter (model HP 53132A, Hewlett Packard, Santa Clara, Calif.), a 400-MHz Time Interval Analyzer (model GT655, Guide Technology Inc., San Jose, Calif.), and a 1-GHz Universal Time Interval Counter (model SR620, Stanford Research Systems, Sunnyvale, Calif.).

The controller 30 is a computer system having inputs, outputs, a memory, and a processor for receiving, sending, storing, and processing signals and data to operate, monitor, record, and otherwise functionally control the operation of the device 10. The controller 30 includes a computer system having an interface board for integrating all of the components of the device 10 and, optionally, a motion controller for controlling the coating and abrasion processes. The controller 30 may include a keyboard for inputting data and commands, a video display for displaying information, and a printer for printing information. The controller 30 may include software, hardware, firmware, and other similar components and circuitry for operating the device 10. The controller 30 may be a single device, or it may be a plurality of devices working in concert. The controller 30 is preferably in communication with all of the other components of the device 10, including the plurality of transducers 12, the plurality of oscillation sources 16, the power source 18, and the oscillation detector(s) 20.

Figure 3:
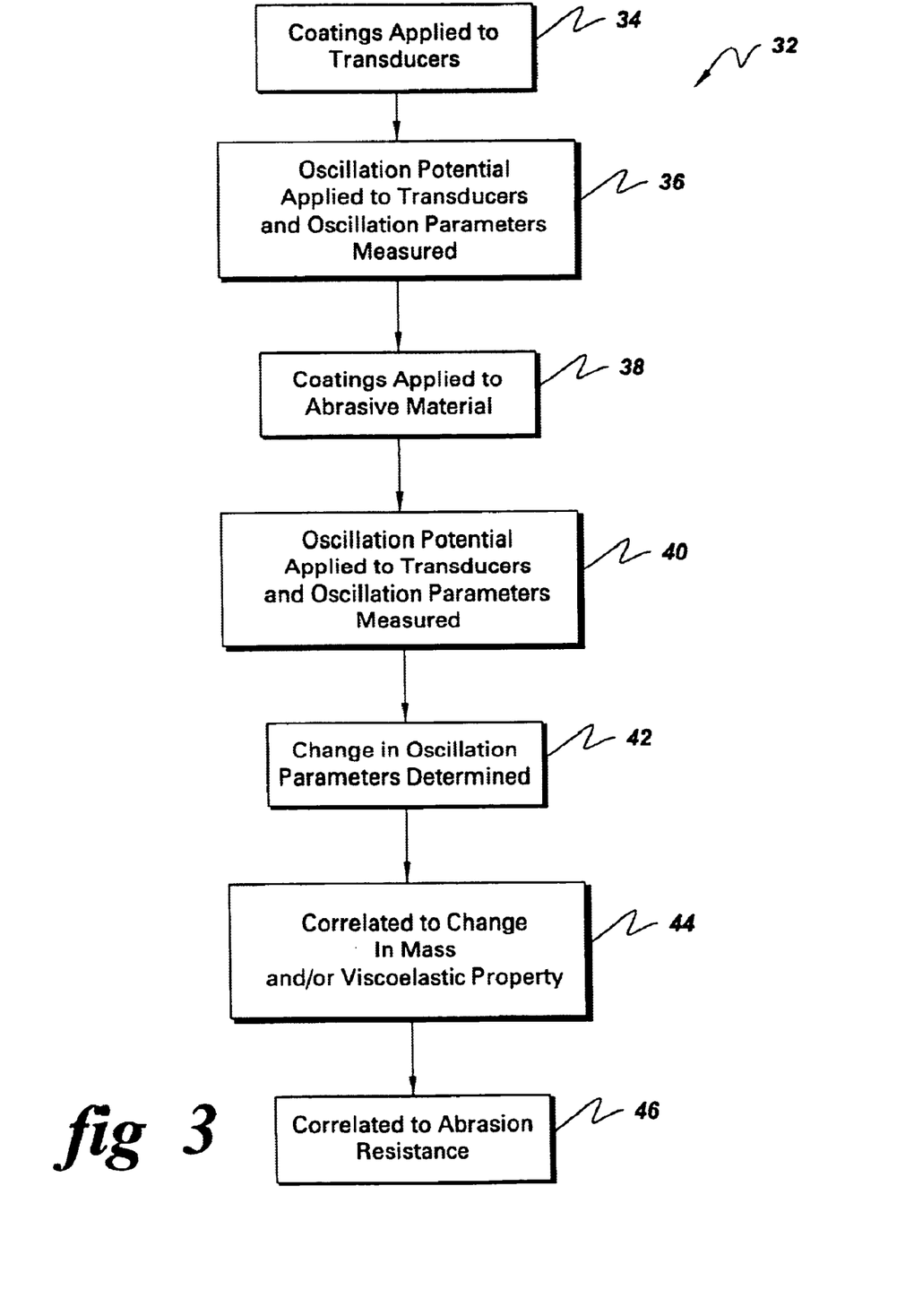
FIG. 3 is a functional block diagram of a method for the high throughput screening of the abrasion resistance of arrays of coatings.

FIG. 3 is a functional block diagram of a method for the high throughput screening of the abrasion resistance of arrays of coatings. Referring to FIG. 3, the method 32 includes providing a plurality of acoustic-wave transducers 12 (FIG. 1), each of the plurality of acoustic-wave transducers 12 having at least one external surface, and depositing a plurality of coatings 14 (FIG. 1) onto the external surface(s) of the plurality of acoustic-wave transducers 12 (Block 34), each of the plurality of coatings 14 deposited onto the external surface(s) of one of the plurality of acoustic-wave transducers 12. As discussed above, the acoustic-wave transducers 12 may be, for example, acoustic-wave TSM transducers 26 (FIG. 2). Further, the method 32 includes generating and applying an oscillation potential to each of the plurality of acoustic-wave transducers 12 and measuring the associated oscillation parameters (Block 36). This is the first oscillation parameter, associated with the unabraded coating 14. The method also includes exposing each of the plurality of coatings 14 to an abrasive material 22 (FIG. 1) (Block 38), the abrasive material 22 causing a change in mass and/or viscoelastic property in each of the plurality of coatings 14, and therefore the coated transducers 12. Finally, the method includes detecting and measuring the second oscillation parameter, associated with the abraded coating, and the variation in oscillation parameter in each of the plurality of transducers 12 (Blocks 40 and 42), wherein the variation in oscillation parameter in each of the plurality of transducers 12 corresponds to the change in mass and/or viscoelastic property in each of the plurality of coatings 14 (Block 44). This change in mass and/or viscoelastic property may then, optionally, be correlated with a traditional measure of abrasion resistance such as a haze measurement (Block 46).

Acoustic-wave transducers may be one or two-port devices. In one-port devices, such as TSM devices, a single port serves as both the input and the output port. The input signal excites an acoustic mode, which in turn generates charges on the input electrode. These signals combine to produce an impedance variation that constitutes the TSM resonator response. In two-port devices, one port is used as the input port and the other as the output port. The input signal generates an acoustic wave that propagates to a receiving transducer which generates a signal on the output port. The relative signal level and phase delay between input and output ports constitute two responses.

Parameters that may be measured using one and two-port acoustic-wave devices include, for example, fundamental oscillation frequency, harmonic oscillation frequency, impedance phase and magnitude (one-port devices), impedance phase and attenuation (two-port devices), wave velocity and wave attenuation, capacitance, and conductance. These parameters relate to the variation in coating mass and/or viscoelastic property upon abrasion testing.

EXAMPLE

AT-cut quartz crystals with gold electrodes were used as TSM transducers. These crystals oscillate in the thickness-shear mode with a fundamental frequency of about 10 MHz. The transducers were arranged in an array of four devices. Coatings were prepared from a mixture of methyltrimethoxysilane and colloidal silica with a level of colloidal silica of about 30%, based upon total solids. The coatings were deposited onto the transducers by dip coating and were cured at about 130° C. for about 30 minutes. The resonant oscillation frequency of the array of transducers was monitored using 225-MHz Universal Counters (model HP 53132A, Hewlett Packard, Santa Clara, Calif.) as a function of time. Data acquisition was performed with a laptop PC using a program written in LabVIEW (National Instruments, Austin, Tex.).

During the abrasion test, the uncoated and coated transducers were exposed to a stream of 50 $\mu$m $Al_2O_3$ particles at a constant pressure and flow applied through a nozzle with an orifice about 1 mm in diameter. The array was automatically advanced under the nozzle with a speed of about 15 cm/min using a single-axis translation stage. The angle of the nozzle was normal to the surface of each TSM transducer. The abrasion test produced an abrased region about 2–3 mm wide across the transducers. An experiment was conducted in which the particle flow rate was held constant and the air pressure varied at about 20 and about 30 psi.

Figure 4:
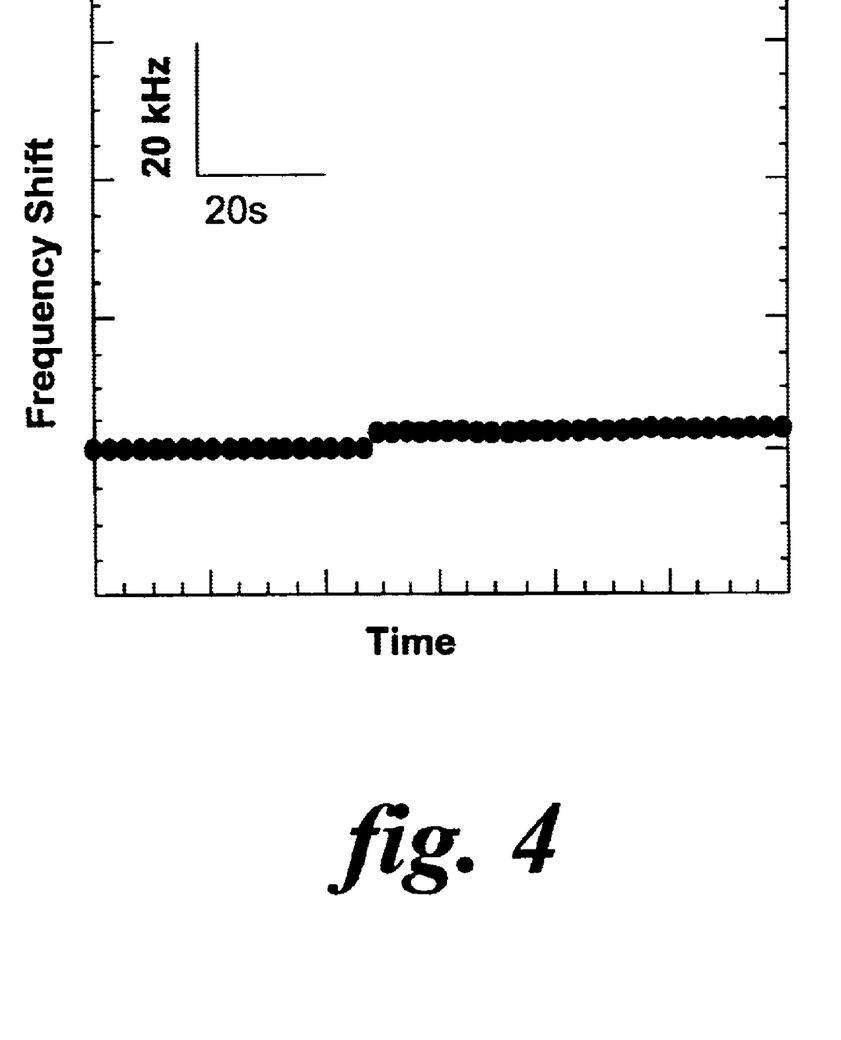
FIG. 4 is a plot of the response of an uncoated transducer to the abrasion test conditions.
Figure 5:
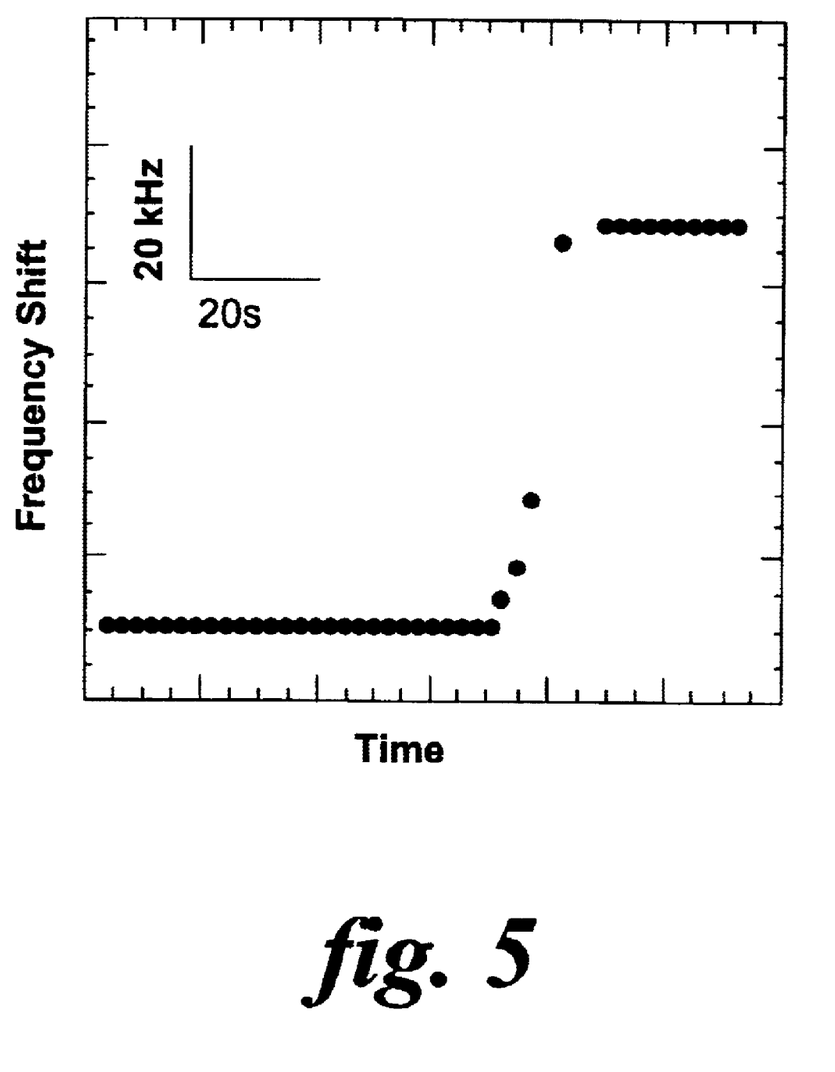
FIG. 5 is a plot of the response of a coated transducer to the abrasion test conditions.

FIG. 4 illustrates a negligible increase in oscillation frequency upon abrasion of an uncoated transducer. In contrast, as shown in FIG. 5, abrasion testing of a coated transducer typically demonstrates a significant increase in oscillation frequency due to the removal of coating.

It is apparent that there has been provided in accordance with the present invention, a device and method for the high throughput screening of the abrasion resistance of arrays of coatings. While the present invention has been particularly shown and described in conjunction with preferred embodiments thereof, it will be appreciated that variations and modifications can be effected by a person of ordinary skill in the art without departing from the spirit or scope of the invention. Further, it is to be understood that the principles related to the selection of transducers and oscillation sources, the methods for applying coatings to the transducers, the detection of applied oscillations and variations in oscillation, and the like, described herein, apply in a similar manner, where applicable, to all embodiments.

What is claimed is:

1. A device for the high throughput screening of the abrasion resistance of coatings, the device comprising:
    a plurality of coatings;
    a plurality of transducers, each of the plurality of transducers having at least one external surface including a deposited one of the plurality of coatings, each of the plurality of transducers having a first oscillation frequency and a second oscillation frequency, the first oscillation frequency corresponding to an unabraded coating and the second oscillation frequency corresponding to an abraded coating;
    a plurality of oscillation sources coupled to the plurality of transducers, each of the plurality of oscillation sources operable for generating and applying an oscillation potential to each of the plurality of transducers; and
    a plurality of oscillation detectors coupled to the plurality of transducers, each of the plurality of oscillation detectors operable for measuring the first oscillation frequency and the second oscillation frequency of each of the plurality of transducers, wherein a variation between the first oscillation frequency and the second oscillation frequency corresponds to a measure of abrasion resistance.

2. The device of claim 1, wherein the variation in oscillation frequency in each of the plurality of transducers corresponds to a change in mass and/or viscoelastic property in each of the plurality of coatings.

3. The device of claim 1, wherein each of the plurality of transducers comprises an acoustic-wave transducer.

4. The device of claim 1, wherein each of the plurality of transducers comprises a thickness-shear mode (TSM) device.

5. The device of claim 1, wherein each of the plurality of transducers comprises a quartz crystal microbalance (QCM).

6. The device of claim 1, further comprising a controller having inputs, outputs, a memory, and a processor for receiving, sending, storing, and processing signals and data to operate, monitor, record, and otherwise functionally control the operation of the device.

7. The device of claim 1, wherein the plurality of coatings comprises a coating array.

8. The device of claim 1, wherein each of the plurality of coatings comprises a mixture of partially hydrolyzed/condensed alkoxy silanes and colloidal silica; a mixture of acrylates, reactively modified colloidal silica and photoinitiator; a mixture of oligomers or monomers containing isocyanate groups and oligomers or monomers containing hydroxyl, amino, or carboxylic acid groups; a mixture of oligomers or monomers containing hydroxyl or N-methylol groups or N-methylol ether groups and oligomers or monomers containing N-methylol groups or N-methylol ether groups or carboxylic acid groups; or a mixture of oligomers or monomers containing epoxide groups and oligomers or monomers containing hydroxyl, amino, carboxylic acid, or anhydride groups, each further mixed with a solvent and various additives.

9. The device of claim 1, further comprising an abrasive material for exposure to each of the plurality of coatings, the abrasive material causing a change in mass in each of the plurality of coatings.

10. The device of claim 9, wherein the abrasive material comprises high grade silica, glass beads, black silicon carbide abrasive powder, boron carbide, diamond powder, aluminum oxide, silicon oxide, garnet, steel grit, walnut shell, sodium bicarbonate, sesquicarbonate, or slurry.

11. The device of claim 1, further comprising a comparative evaluation of the abrasion resistance performance of the plurality of coatings.

12. A device for the high throughput screening of the abrasion resistance of coatings, the device comprising:
    a plurality of coatings;
    a plurality of transducers, each of the plurality of transducers having at least one external surface including a deposited one of the plurality of coatings, each of the plurality of transducers having a first oscillation frequency and a second oscillation frequency, the first oscillation frequency corresponding to an unabraded coating and the second oscillation frequency corresponding to an abraded coating;
    a plurality of oscillation sources coupled to the plurality of transducers, each of the plurality of oscillation sources operable for generating and applying an oscillation potential to each of the plurality of transducers;
    a plurality of oscillation detectors coupled to the plurality of transducers, each of the plurality of oscillation detectors operable for measuring the first oscillation frequency and the second oscillation frequency of each of the plurality of transducers, wherein a variation between the first oscillation frequency and the second oscillation frequency corresponds to a measure of abrasion resistance; and
    an abrasive material for exposure to each of the plurality of coatings, the abrasive material causing a change in mass in each of the plurality of coatings.

13. The device of claim 12, wherein the variation in oscillation frequency in each of the plurality of transducers corresponds to the change in mass in each of the plurality of coatings.

14. The device of claim 12, wherein each of the plurality of transducers comprises an acoustic-wave transducer.

15. The device of claim 12, wherein each of the plurality of transducers comprises a thickness-shear mode (TSM) device.

16. The device of claim 12, wherein each of the plurality of transducers comprises a quartz crystal microbalance (QCM).

17. The device of claim 12, further comprising a controller having inputs, outputs, a memory, and a processor for receiving, sending, storing, and processing signals and data to operate, monitor, record, and otherwise functionally control the operation of the device.

18. The device of claim 12, wherein the plurality of coatings comprises a coating array.

19. The device of claim 12, wherein each of the plurality of coatings comprises a mixture of partially hydrolyzed/condensed alkoxy silanes and colloidal silica; a mixture of acrylates, reactively modified colloidal silica and photoinitiator; a mixture of oligomers or monomers containing isocyanate groups and oligomers or monomers containing hydroxyl, amino, or carboxylic acid groups; a mixture of oligomers or monomers containing hydroxyl or N-methylol groups or N-methylol ether groups and oligomers or monomers containing N-methylol groups or N-methylol ether groups or carboxylic acid groups; or a mixture of oligomers or monomers containing epoxide groups and oligomers or monomers containing hydroxyl, amino, carboxylic acid, or anhydride groups, each further mixed with a solvent and various additives.

20. The device of claim 12, wherein the abrasive material comprises high grade silica, glass beads, black silicon carbide abrasive powder, boron carbide, diamond powder, aluminum oxide, silicon oxide, garnet, steel grit, walnut shell, sodium bicarbonate, sesquicarbonate, or slurry.

21. The device of claim 12, further comprising a comparative evaluation of the abrasion resistance performance of the plurality of coatings.

22. A method for the high throughput screening of the abrasion resistance of coatings, the method comprising:
    generating and applying an oscillation potential to each of a plurality of transducers having one of a plurality of coatings deposited onto at least one surface; and
    detecting and measuring a first oscillation parameter and a second oscillation parameter of each of the plurality of transducers, wherein the first oscillation parameter corresponds to an unabraded coating, the second oscillation parameter corresponds to an abraded coating, and a variation between the first oscillation parameter and the second oscillation parameter corresponds to a measure of abrasion resistance.

23. The method of claim 22, further comprising providing a plurality of transducers, each of the plurality of transducers having at least one external surface.

24. The method of claim 22, further comprising depositing a plurality of coatings onto the external surface(s) of the plurality of transducers, each of the plurality of coatings deposited onto the external surface(s) of one of the plurality of transducers.

25. The method of claim 22, further comprising exposing each of the plurality of coatings to an abrasive material, the abrasive material causing a change in mass in each of the plurality of coatings.

26. The method of claim 25, wherein the abrasive material comprises high grade silica, glass beads, black silicon carbide abrasive powder, boron carbide, diamond powder, aluminum oxide, silicon oxide, garnet, steel grit, walnut shell, sodium bicarbonate, sesquicarbonate, or slurry.

27. The method of claim 22, wherein the variation in oscillation parameter in each of the plurality of transducers corresponds to a change in mass and/or viscoelastic property in each of the plurality of coatings.

28. The method of claim 22, wherein the measured parameters comprise parameters selected from the group consisting of fundamental oscillation frequency, harmonic oscillation frequency, impedance phase and magnitude, impedance phase and attenuation, wave velocity and wave attenuation, capacitance, and conductance.

29. The method of claim 22, wherein providing a plurality of transducers comprises providing a plurality of acoustic-wave transducers.

30. The method of claim 22, wherein providing a plurality of transducers comprises providing a plurality of thickness-shear mode (TSM) devices.

31. The method of claim 22, wherein providing a plurality of transducers comprises providing a plurality of quartz crystal microbalances (QCMs).

32. The method of claim 22, wherein the plurality of coatings comprises a coating array.

33. The method of claim 22, wherein each of the plurality of coatings comprises a mixture of partially hydrolyzed/condensed alkoxy silanes and colloidal silica; a mixture of acrylates, reactively modified colloidal silica and photoinitiator; a mixture of oligomers or monomers containing isocyanate groups and oligomers or monomers containing hydroxyl, amino, or carboxylic acid groups; a mixture of oligomers or monomers containing hydroxyl or N-methylol groups or N-methylol ether groups and oligomers or monomers containing N-methylol groups or N-methylol ether groups or carboxylic acid groups; or a mixture of oligomers or monomers containing epoxide groups and oligomers or monomers containing hydroxyl, amino, carboxylic acid, or anhydride groups, each further mixed with a solvent and various additives.

34. The method of claim 22, further comprising performing a comparative evaluation of the abrasion resistance performance of the plurality of coatings.

35. A method for the high throughput screening of the abrasion resistance of coatings, the method comprising:
    providing a plurality of transducers, each of the plurality of transducers having at least one external surface;
    depositing a plurality of coatings onto the external surface(s) of the plurality of transducers, each of the plurality of coatings deposited onto the external surface(s) of one of the plurality of transducers;
    exposing each of the plurality of coatings to an abrasive material, the abrasive material causing a change in mass in each of the plurality of coatings;
    generating and applying an oscillation potential to each of the plurality of transducers having one of a plurality of coatings deposited onto at least one surface; and
    detecting and measuring a first oscillation frequency and a second oscillation frequency of each of the plurality of transducers, wherein the first oscillation frequency corresponds to an unabraded coating, the second oscillation frequency corresponds to an abraded coating, and a variation between the first oscillation frequency and the second oscillation frequency corresponds to a measure of abrasion resistance.

36. The method of claim 35, wherein the variation in oscillation in each of the plurality of transducers corresponds to a change in mass in each of the plurality of coatings.

37. The method of claim 35, wherein providing a plurality of transducers comprises providing a plurality of acoustic-wave transducers.

38. The method of claim 35, wherein providing a plurality of transducers comprises providing a plurality of thickness-shear mode (TSM) devices.

39. The method of claim 35, wherein providing a plurality of transducers comprises providing a plurality of quartz crystal microbalances (QCMs).

40. The method of claim 35, wherein the plurality of coatings comprises a coating array.

41. The method of claim 35, wherein each of the plurality of coatings comprises a mixture of partially hydrolyzed/condensed alkoxy silanes and colloidal silica; a mixture of acrylates, reactively modified colloidal silica and photoinitiator; a mixture of oligomers or monomers containing isocyanate groups and oligomers or monomers containing hydroxyl, amino, or carboxylic acid groups; a mixture of oligomers or monomers containing hydroxyl or N-methylol groups or N-methylol ether groups and oligomers or monomers containing N-methylol groups or N-methylol ether groups or carboxylic acid groups; or a mixture of oligomers or monomers containing epoxide groups and oligomers or monomers containing hydroxyl, amino, carboxylic acid, or anhydride groups, each further mixed with a solvent and various additives.

42. The method of claim 35, wherein the abrasive material comprises high grade silica, glass beads, black silicon carbide abrasive powder, boron carbide, or a diamond powder, compound, or slurry.

43. The method of claim 35, further comprising performing a comparative evaluation of the abrasion resistance performance of the plurality of coatings.

* * * * *